US006481300B1

(12) United States Patent
Cordry

(10) Patent No.: US 6,481,300 B1
(45) Date of Patent: Nov. 19, 2002

(54) NO PURGE SAMPLER

(76) Inventor: Kent E. Cordry, 308 Mountaire Pkwy., Clayton, CA (US) 94517

(*) Notice: Subject to any disclaimer, the term of this patent is extended or adjusted under 35 U.S.C. 154(b) by 0 days.

(21) Appl. No.: 09/569,817

(22) Filed: May 12, 2000

(51) Int. Cl.$^7$ ................................................. G01N 1/12
(52) U.S. Cl. ........................... 73/864.65; 73/864; 73/63
(58) Field of Search ......................... 73/864.63, 864.62, 73/864.65, 864.66, 864.64; 166/264

(56) References Cited

U.S. PATENT DOCUMENTS

| | | | | |
|---|---|---|---|---|
| 4,050,315 A | * | 9/1977 | Markfelt | 73/425.4 R |
| 4,157,664 A | * | 6/1979 | Robinson | 73/864.64 |
| 4,254,830 A | * | 3/1981 | Garney et al. | 166/162 |
| 4,266,429 A | * | 5/1981 | Brovold | 73/425.4 R |
| 4,271,704 A | * | 6/1981 | Peters | 73/864.63 |
| 5,454,275 A | * | 10/1995 | Kabis | 73/864.51 |
| 5,507,194 A | * | 4/1996 | Scavuzzo et al. | 73/864.63 |
| 5,753,831 A | * | 5/1998 | Mohs | 73/864.63 |
| 5,878,813 A | * | 3/1999 | Ridgeway, Jr. | 166/162 |
| 5,902,940 A | * | 5/1999 | Stern | 73/864.63 |
| 6,167,962 B1 | * | 1/2001 | Pratt | 166/162 |

OTHER PUBLICATIONS

Alexander et al., "Field Trial of a New Commercially Available Diffusive Ground–Water Sampler," Bunnell–Lammons Engineering, Inc., Greensville, South Carolina, 6pp.
Eon Products, Inc., Lithonia, Georgia, "EON GrounDwater Diffusion Sampler" brochure, 2pp.
Eon Products, Inc., Lithonia, Georgia, "EON Diffusion Sampler" brochure, 1 page.
Horton et al., "The California Groundwater Purging Study for Petroleum Hydrocarbons," *Proceedings of the Eleventh National Outdoor Action$^{SM}$ Conference and Exposition*, Las Vegas, Nevada, Apr. 1–3, 1997, pp. 109–122.
QED GroundWater Specialist, "Micro Purge" brochure, pp. 3–5.
Vroblesky et al., "Diffusion Samplers as an Inexpensive Approach to Monitoring VOCs in Ground Water," *GWMR*, Summer 1997, pp. 177–184.

* cited by examiner

*Primary Examiner*—Hezron Williams
*Assistant Examiner*—Charles Garber
(74) *Attorney, Agent, or Firm*—Christie, Parker & Hale, LLP

(57) ABSTRACT

A no purge sampler for collecting fluid samples includes a flexible tube having a sealed first end and a second end, the tube defining an interior cavity, a buoyancy-compensating ballast compartment secured to the tube, and a check valve disposed at the second end of the tube. To collect fluid samples, the no purge sampler is lowered into the fluid to be sampled. The buoyancy-compensating ballast compartment is filled with an appropriate ballast to allow the sampler to sink to a desired level. Once the sampler reaches the desired depth, the sampler is moved up and down to pump water into the collapsed tube. The check valve is opened each time the sampler is pulled upwards allowing fluid to enter the interior cavity. The up and down motion is repeated until the interior cavity of the tube is filled with fluid. Once the interior cavity is filled, the pressure of the fluid in the tube causes the check valve to close, thereby preventing additional fluid from entering the interior cavity. The sampler is then pulled out of the fluid without losing any of the fluid in the interior cavity of the tube or the sample contaminated with any extraneous fluid.

9 Claims, 4 Drawing Sheets

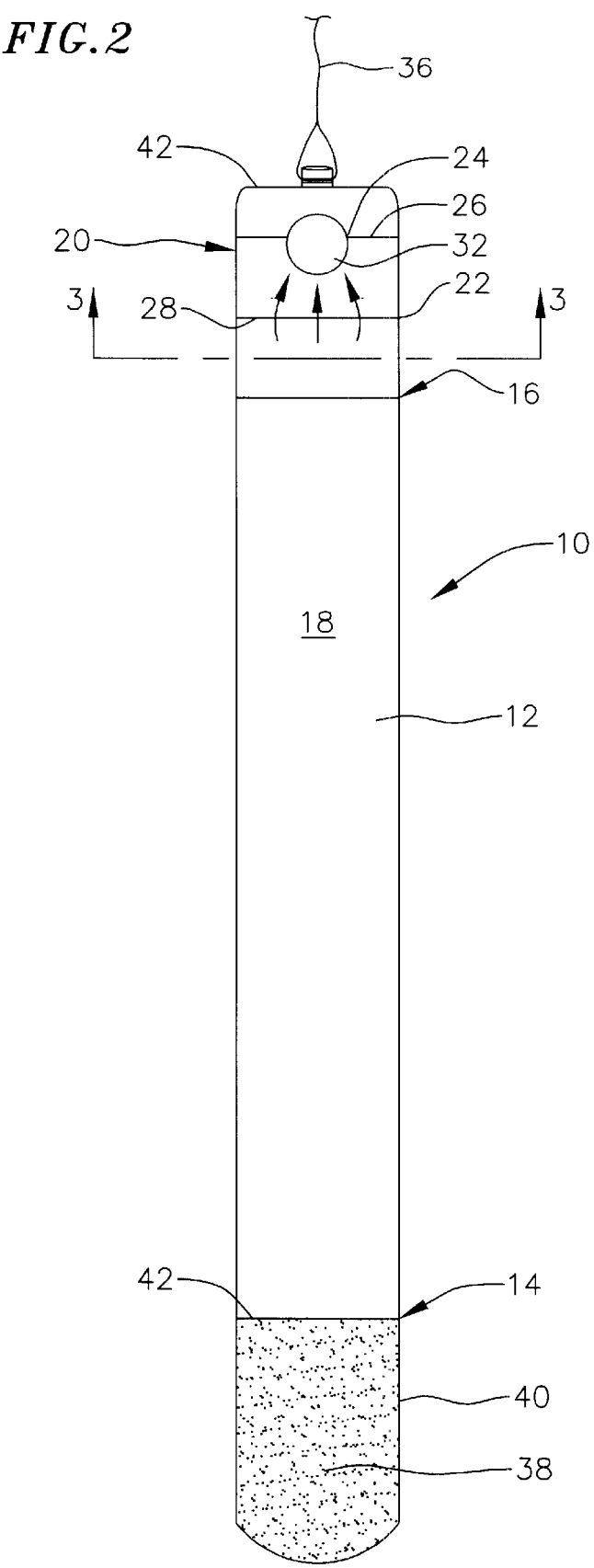
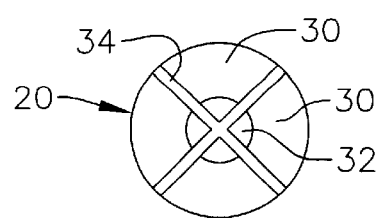

*FIG.5*
*FIG.6*
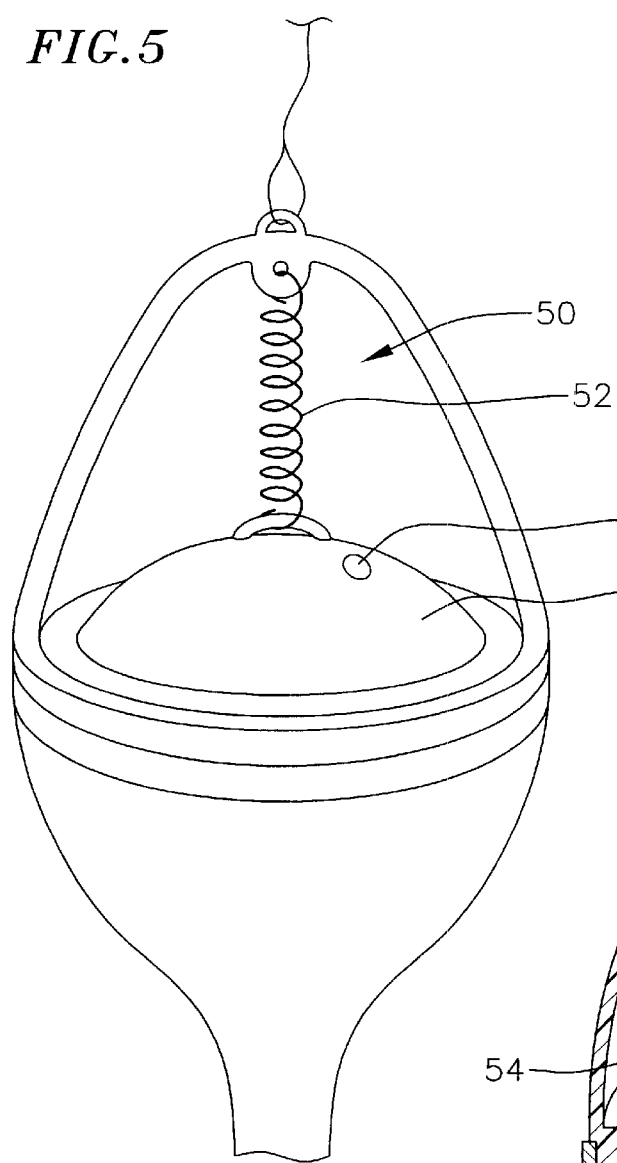
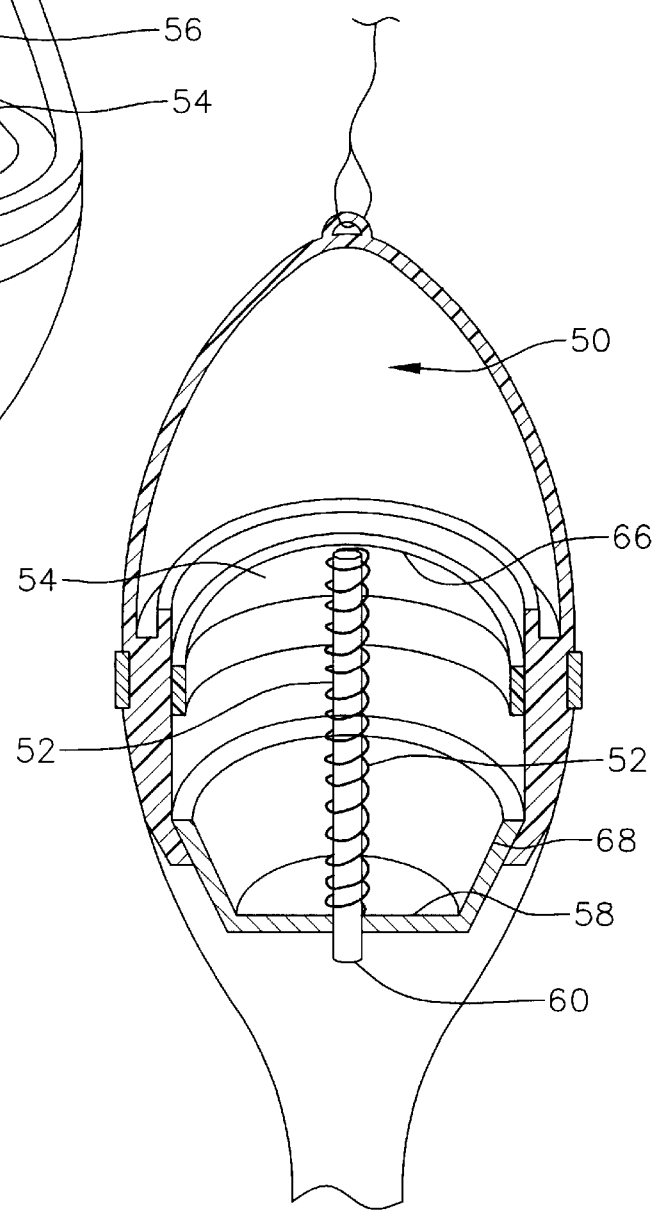

NO PURGE SAMPLER

FIELD OF THE INVENTION

This invention generally relates to sampling devices used for sampling water in a groundwater well and collecting an unaltered water sample from a specific water strata. More particularly, the invention relates to a disposable grab sampler that eliminates the need for purging yet provides a representative sample of groundwater from monitoring wells during the sampling process.

BACKGROUND OF THE INVENTION

The conventional practice of purging water during the process of sampling water found in a groundwater monitoring well is based on the need to remove stagnant water from the portion of the well that is not open to the water bearing formation prior to sampling. It is thought that this stagnant water is not representative of the in-situ water quality and, therefore, must be removed before any type of accurate sampling process can be allowed to proceed. Traditional practices of bailing or high-rate pumping of water from a well during the purging process necessitate the removal of multiple "well volumes" to ensure adequate removal of all stagnant water from the sampling zone. For instance, in a known procedure for sampling ground water monitoring wells, three to five times the volume of the standing water in a well screen, casing and surrounding filter pack is removed prior to collecting a sample to assure that only unaltered formation water is tested.

The use of traditional sampling devices and pumping systems, to conduct groundwater monitoring results in a time consuming and costly sampling process. The use of samplers, such as bailers, portable pumps, and high speed pumps mixes the stagnant water in the well casing with the "fresh" water in the screened interval. Moreover, high-rate pumping of water from the well can induce drawdown within the well and surrounding formation, causing stagnant water to be mixed with incoming water and contaminating the samples. High-volume purging often requires hours to complete, and results in the creation of tens or hundreds of gallons of purge water which often must be contained for disposal as a liquid hazardous waste.

The cost of properly disposing of groundwater that qualifies as a hazardous material further adds to the cost of the sampling process. It would therefore be desirable to minimize the amount of water that is required to be removed prior to collecting the water sample, yet still provide a representative sample.

Several methods have been proposed to deal with this specific problem. One of the methods that has been gaining acceptance in the groundwater monitoring community is the "low flow" sampling process. Low flow sampling is the process of pumping a monitoring well at a very low flow rate before sampling to eliminate the mixing of stagnant water above the screened interval with the fresh water in the screened interval. During low flow sampling, a very limited volume of water is removed from the well, resulting in minimal drawdown of the water column within the well. Low flow sampling is based on the rationale that a screened section of a well casing has fresh formation water flowing through it at a rate equal to the rate it moves through the aquifer. Water in a non-screened section of the well casing, above the screened section, is stagnant and thus not representative of in-situ well water conditions. Low flow sampling focuses on removing water only from the screened interval.

The low flow sampling process requires that a dedicated pump be left in the well for sampling purposes. The pump is lowered into the well and is positioned in the screened section of the well. As the pump is lowered downwardly through the well, it first passes through the stagnant water existing in the non-screened section of the well casing. As it is lowered, it mixes the stagnant water with the fresh formation water in the screened zone of the well below. Because of this initial mixing, the pump must sit undisturbed within the screened section of the well until the well once again reaches equilibrium. After equilibrium is reached, usually in a matter of days, sampling can begin. The pump is started and water is withdrawn from the well at a rate which does not result in draw down of the water level and mixing of the stagnant water into the well screened section. As the water is slowly pumped from the well, it is monitored for stabilization of indicator parameters. As soon as the parameters are stabilized, indicating that the pumping system has been purged of extraneous water and that the withdrawn water is coming from the formation, a sample is collected.

The disadvantages of the low flow sampling process are that it is often slow and complex and requires specialized training of the sampling personnel. Moreover, the capital costs associated with the equipment used to conduct low flow sampling is high. The dedicated pump and tubing are costly and additional surface instrumentation further adds to the cost of the procedure. Accordingly, there is a need for a sampling device that is quick and easy to use that does not require extensive training of the field personnel. Moreover, it is desirable to have a sampling device that does not require costly equipment to operate.

Another known sampling method that has been proposed is the "no purge" sampling method that is carried out by using a conventional sampler. Like the low flow sampling method, the no purge concept is based on the premise that a well's intake screen and filter pack are more permeable than the formation being sampled, and that because of this, water is constantly flowing through the well's screened section. If there is no stagnant water in the well casing, as when the top of the screened section is positioned above the top of the water table, it is proposed that purging is not needed. A conventional bailer is dropped into the water column and a sample of groundwater is immediately collected. To successfully use this procedure, however, the screened section of the well casing must extend above the water table, thereby eliminating the presence of stagnant water that could mix with the formation water as the bailer is lowered. The absence of such stagnant water eliminates the prospect of the recovered bailed water sample becoming contaminated.

A newer sampling method is "diffusion" sampling. Diffusion sampling is a passive sampling process that is conducted by using a sealed polyethylene bag filled with water that is lowered into the screened section of a monitoring well. Molecular diffusion of volatile organic contaminants (VOC's) causes chemical equilibrium to occur between the water in the sampler and the water in the well. After allowing approximately 14 days for the concentrations to equilibrate, the sampler is withdrawn and the water in the bag is removed and analyzed. This method has limited applicability, however, as only specific types of contaminants diffuse through the polyethylene bag and different contaminants diffuse at different rates. Accordingly, a need exists for a sampling device that has broad applicability

SUMMARY OF THE INVENTION

The present invention overcomes the aforementioned problems by providing a no purge "thief" or "grab" sampler which is disposable, inexpensive and easy to operate. The no purge sampler of the present invention eliminates purge water and minimizes labor costs associated with the sampling process. Accordingly, the cost of disposing hazardous liquid waste is minimized, if not eliminated.

The no purge sampler for collecting fluid samples, constructed according to the present invention, includes a tube having a sealed first end and a second end, the tube defining an interior cavity, a buoyancy-compensating ballast compartment secured to the tube, and a check valve disposed at the second end of the tube. The tube is preferably is made of a flexible, pliant material. To collect fluid samples, the no purge sampler is lowered into the fluid to be sampled. The buoyancy-compensating ballast compartment is filled with an appropriate ballast to allow the sampler to sink to a desired level. In one embodiment of the present invention, the ballast is sand. Once the sampler reaches the desired depth, the sampler is moved up and down to pump water into the tube. The check valve is opened each time the sampler is pulled upwardly, allowing fluid to enter the interior cavity. The up and down motion is repeated until the interior cavity of the tube is fully expanded and filled with fluid. Once the interior cavity is filled, the pressure of the fluid in the tube causes the check valve to close, thereby preventing additional fluid from entering the interior cavity. The sampler is then pulled out of the fluid without losing any of the fluid in the interior cavity of the tube or allowing additional fluid to enter the sampler.

The check valve disposed within the sampler can be of any type, including, but not limited to, a floating ball-type check valve, collapsing reed valve, and lift check valve and the like. The check valve remains closed when the sampler is lowered into the fluid to be sampled. The check valve opens when the sampler is pulled upward and it is subjected to a fluid pressure differential across it and closes again on the downstroke. When the interior cavity of the tube is filled with the sampled fluid, the check valve remains closed, thereby preventing additional unwanted fluid from entering the cavity as the sampler is recovered from the well through the overlying water column.

The no purge sampler can be made of any diameter or length to accommodate a desired sample volume or well size. The no purge sampler may be constructed from any pliant material depending on the application. The dimensions of the sampler are dependent on the application in which it is utilized. Although the no purge sampler of this invention is preferably used to collect groundwater samples from discrete intervals within wells, it could also be used to sample fluid from streams, oceans, lakes, storage tanks or any other fluid bearing medium.

No purge samplers of the present invention require a simple operating procedure. Unlike previously known sampling devices, there is no need for extensive training of field personnel to utilize the no purge sampler of the present invention. Moreover, no purge samplers of the present invention are inexpensive to produce and do not require costly equipment to operate. Finally, unlike the diffusion sampler described above, no purge samplers of this invention have broad applicability and are not limited the sampling of fluids containing specific types of contaminants.

This invention, together with the additional features and advantages thereof, which was only summarized in the foregoing passages, will become more apparent to those of skill in the art upon reading the description of the preferred embodiments, which follows in the specification, taken together with the following drawings.

DESCRIPTION OF THE DRAWINGS

FIG. 2 is a schematic cross-sectional side view of the invention of FIG. 1, wherein the interior cavity of the tube has been filled with a sample fluid and the check valve is shown in a closed position, preventing further fluid from entering the interior cavity of the tube;

FIG. 3 is a cross-sectional end view of the check valve of the present invention taken along line 3—3 of FIG. 2;

FIG. 5 is a semi-schematic perspective view of an exemplary embodiment of the sampler of the present invention wherein the check valve is spring biased in a closed position; and FIG. 6 is a semi-schematic perspective view of an exemplary embodiment of the sampler of the present invention wherein the check valve is spring biased in a closed position.

DETAILED DESCRIPTION OF THE INVENTION

Figure 1:
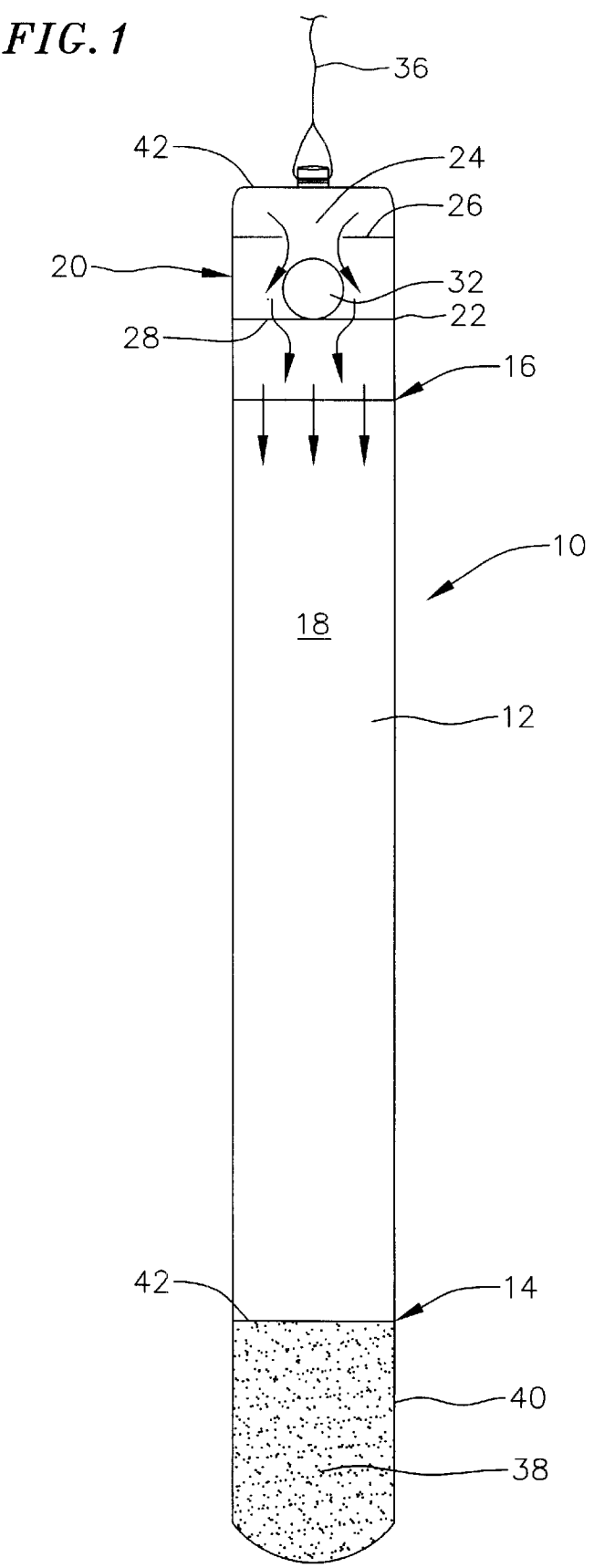
FIG. 1 is a schematic cross-sectional side view illustrating one embodiment of the invention comprising a tube having a sealed first end and a check valve disposed at a second end shown in an open position for regulating the flow of sample fluid into an interior cavity of the tube.

Referring to the drawings, wherein like reference numerals designate identical or corresponding parts throughout the views and embodiments, an exemplary embodiment of a no purge sampler according to the principles of the present invention is illustrated in FIGS. 1 and 2 and identified by reference numeral 10.

Referring to FIGS. 1 and 2, the no purge sampler 10 of the present invention includes a flexible tube 12 having a first end 14 and a second end 16. In the illustrated embodiment, the first end 14 is disposed below the second end 16 when the sampler 10 is held in a vertical position, as shown in FIGS. 1 and 2. The tube 12 is preferably constructed of a flexible polymeric material sheet or film, e.g., polyethylene, and defines an interior cavity 18 for collecting fluid samples therein. In a preferred embodiment of the present invention, the tube 12 has a thickness of approximately 4 mm. The material used to construct tube 12 is preferably transparent to allow visual inspection of the collected sample. The first end 14 of tube 12 is sealed and the second end 16 is open providing an access or pathway for the sample being collected to enter the interior cavity 18 of the tube.

The sample fluid enters the cavity 18 through a check valve disposed on the second end 16 of tube 12. In the preferred embodiment, the check valve is a floating ball type check valve 20, as shown in FIGS. 1 and 2. The check valve is preferably dome-shaped so water drains off the check valve during removal. In this embodiment, the outer edge 22 of check valve 20 is sealably connected around the inside surface of the tube's second end 16 to thereby prevent any fluid from flowing into the interior cavity 18 around the check valve's outer edge. The check valve 20 has a first plateau 26 and a second plateau 28 preferably positioned beneath the first plateau. In the preferred embodiment, the first plateau is ring-shaped with an inlet opening 24 in its center through which the collected fluid first enters the sampler. The second plateau 28 is also preferably ring-shaped and includes a plurality of openings 30, as shown in FIG. 3, that allow the collected fluid entering the sampler to flow into the interior cavity 18 of tube 12.

A check ball 32 is confined between the first and second plateaus 26 and 28. The width of the inlet opening 24 of the first plateau 26 is dimensioned to be less than the diameter of the check ball 32 such that when the check ball is pressed up against the inlet opening 24 under an exerted force, the inlet opening is closed and no fluid is permitted to enter the interior cavity. Furthermore, the inlet opening 24 prevents the check ball 32 from exiting the sampler 10 since the diameter of the check ball is too large to fit through the inlet opening 24. The second plateau 28 includes barrier members 34, best shown in FIG. 3, that prevent check ball 32 from entering the interior cavity 18 of tube 12. FIG. 1 illustrates the check ball 32 in a position adjacent to the second plateau 28. When the check ball 32 is in this position, the inlet opening 24 is open allowing sample fluid to enter the check valve 20. FIG. 2 illustrates the check ball 32 blocking the inlet opening 24 thereby preventing fluid from entering the valve. The check valve 20, including the check ball 32, is preferably made of a material that is resistant to corrosion caused by the contaminants that may be found in the sample fluid. For example, the check valve and ball may be made of various plastics, such as polypropylene, polyethylene, impact polystyrene, or ABS or the like. The check ball has a density less than the density of the fluid being sampled. The check ball floats such that it is seated in the opening 24 when the sampler is full.

In operation, the no purge sampler 10 is guided into the fluid from which a sample is desired. A suspension line 36 and ballast 38 can be used to assist with the submersion of the sampler 10 in the fluid. In one embodiment, the suspension line 36 is connected to a submersion handle 42 mounted on the top of the sampler. In a preferred embodiment, a buoyancy-compensating ballast compartment 40 is secured to the first end 14 of tube 12. The buoyancy-compensating ballast compartment 40 is filled with an appropriate ballast 38 to allow the sampler to sink to a desired level. One type of ballast that can be used is an inexpensive sand that is free from contaminants and soluble salts. In a preferred embodiment, the ballast is a steel weight, preferably triple sealed to protect against corrosion and interference with the sample water. The ballast is preferably isolated from the sample tube 12 by the ballast compartment 40. In one embodiment, the ballast is installed in the bottom end of the tube 12, and a heat seal 42 is formed in the tube to define the top of the ballast compartment. In another embodiment, the ballast compartment 40 is detachable from tube 12 and can be reused with other samplers.

Figure 4A:
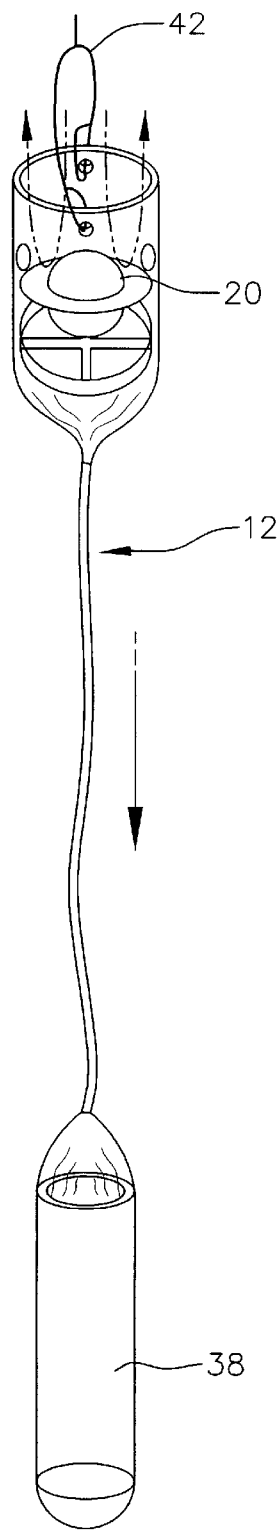
FIGS. 4a through 4c illustrate the operation of the sampler of the present invention.
Figure 4B:
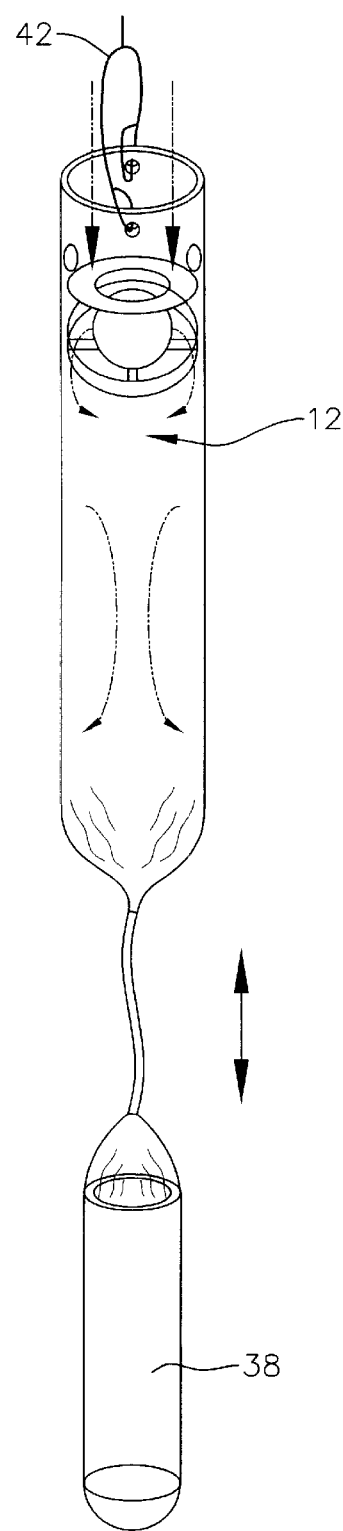
Figure 4C:
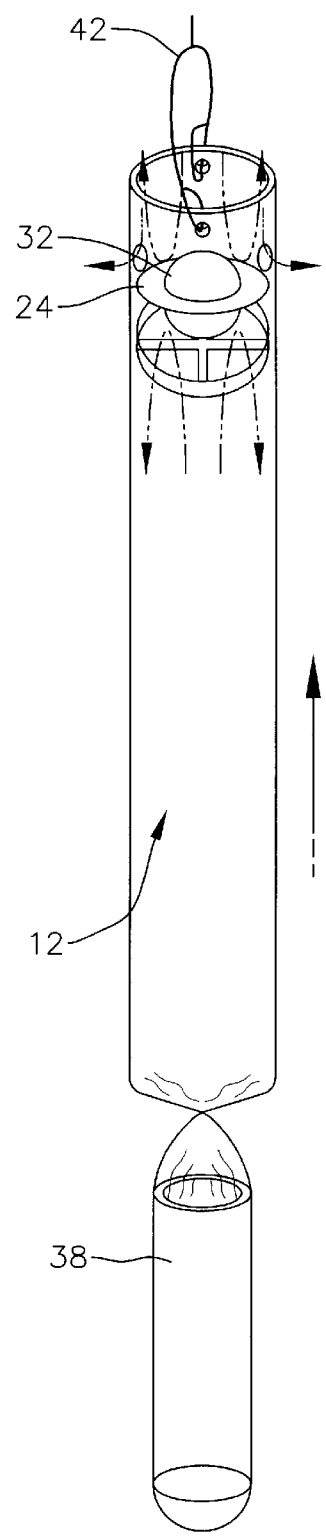

The operation of one embodiment of the sampler for collecting a sample of ground water from a monitoring well is best shown in FIGS. 4a through 4c. To collect the ground water sample, the no purge sampler 10 is lowered into the fluid in the well being sampled. As the sampler is lowered into the well, the check valve 20 remains closed and hydrostatic pressure collapses the flexible tube 12, as shown in FIG. 4a. The slim profile minimizes mixing of water within the well. During the submersion phase of the sampling operation, no fluid can flow into the sampler because the check ball 32 blocks the inlet opening 24. Once the well has returned to equilibrium, a sample can be collected.

During the sampling phase of the operation, the sampler is moved up and down in the screened section of the well to pump water into the flexible tube. The check valve 20 opens each time the sampler is pulled upwards allowing water to enter the interior cavity 18 via the opening 24. The up and down motion is repeated until the interior cavity 18 of the tube is filled with water. In the preferred embodiment, the sampler is manually raised and lowered about 6 inches using the suspension line. The cycle is preferably repeated a minimum of 20 times. On the upstroke, the upper check valve 20 opens and water moves into the tube 12, expanding it, as shown in FIG. 4b. During the down cycle, the check valve 20 closes trapping the sample in the tube. The next upstroke repeats the process, which continues until the tube is full.

The flexible tube preferably has a degree of elasticity such that when the tube is full, the tube exerts pressure on the fluid in an attempt to return to its original volume. The pressure of the water in the tube causes the check valve to remain closed, as shown in FIG. 4C, thereby preventing additional water from entering the cavity. The check valve floats such that it stays seated when the tube is full. The sampler is then pulled out of the screened section of the well without losing any of the sample water in the tube and without allowing extraneous water into the sampler during recovery.

Check valves used in the present invention can be of any type, including, but not limited to, a floating ball-type check valve 22 (as shown in FIGS. 1–3), collapsing reed valves, flapper valves, lift check valves and the like. The check valve must remain closed when being submerged into the fluid to be sampled. The check valve must then be opened when it is pulled upward and closed again on the downstroke. When the interior cavity of the tube is filled with the sampled fluid, the check valve remains closed, thereby preventing additional fluid from entering the cavity and allowing the sampler to be removed from the fluid to be sampled without losing any of the fluid in the interior cavity itself. The check valve is preferably dome-shaped for better water drainage.

In a preferred embodiment of the present invention, as shown in FIGS. 5 and 6, a check valve 50 is biased in a closed position by spring 52. During the initial submersion, the check valve 50 remains closed as a result of the spring force. In this phase, no fluid will be able to flow into the sampler because the dome 54 of the check valve 50 blocks the inlet opening 24. Once the well has returned to equilibrium, the sampler is moved up and down to pump water into the tube in the same manner as described above with reference to the embodiments of FIGS. 1–4. When the sampler is pulled upwards, the force of the water on the check valve counteracts the spring force, causing the dome 54 of the check valve 50 to be separated from the inlet opening 24. Thus, the check valve 50 is opened each time the sampler is pulled upwards allowing fluid to enter the interior cavity 18.

Once the interior cavity 18 is filled, the back pressure of the fluid in the tube, in addition to the force of the spring 52, causes the check valve 50 to remain closed thereby preventing additional fluid from entering the interior cavity 18. When the tube is full, the check valve 50 remains closed as the sampler is pulled out of the fluid, without losing any of the fluid in the interior cavity of the tube and without allowing extraneous fluid into the sampler during recovery.

The spring 52, as shown in FIG. 5, is attached between the submersion handle 42 and the check valve 50. As discussed above, the spring is configured to bias the check valve 50 in a closed position yet allow the check valve to open when counteracted with pressure exerted by fluid as the sampler is moved upward. In this embodiment, the check valve preferably has a hollow semi-spherical shape, forming a dome 54. The dome 54 of the check valve 50 preferably has an air vent hole 56 therein such that the trapped air inside the tube can exit through the vent hole.

Alternatively, as shown in FIG. 6, the spring 52 can be placed between the check valve 50 and a spring seat 58. In this embodiment, a first end 62 of the spring 52 is seated on the underside 66 of the dome 54. The second end 64 of the spring 52 is seated on the spring seat 58. The spring seat 58 is preferably attached to the sides 68 of the sampler. A support bar 60 is attached on the underside 66 of the dome 54 to align the spring 52. The spring is configured to bias the check valve 50 in a closed position when the sampler is lowered into the water or when it is at rest. When the sampler is moved upward, however, the pressure exerted by the water on the check valve causes the check valve to open, allowing the water to enter the tube.

The samplers of the present invention can be made of any diameter or length to accommodate a desired sample volume or well size. The dimensions of the sampler are dependent on the application in which it is utilized. Although no purge samplers of this invention are preferably used to collect groundwater samples from discrete intervals within wells, they can also be used to sample fluids from streams, oceans, lakes, storage tanks or any other fluid bearing medium.

As described above, the operating procedure of the no purge sampler 10 of the present invention is simple. Unlike previously known sampling devices, there is no need for extensive training of field personnel to utilize the no purge sampler described herein. Moreover, the no purge sampler of the present invention is inexpensive to produce and does not require costly equipment to operate. The sampler is disposable, thus eliminating errors resulting from contaminants that may remain in the sampler from previous sampling events. The low cost of the samplers will deter covert reuse of disposable samplers. Finally, unlike the diffusion sampler described above, the no purge sampler 10 has broad applicability and is not limited the sampling of fluids containing specific types of contaminants.

It is to be understood that various modifications can be made to the disclosed embodiments of the present invention without departing from the spirit and scope thereof. For example, various sizes of the no purge sampler and particularly, various tubing diameters, are contemplated as well as various types of valve, tube and ballast materials and components. Also, various modifications may be made to the configuration of the parts and their interaction. Therefore, the above description should not be construed as limiting the invention, but merely as an exemplification of preferred embodiments thereof. Those of skill in the art will envision other modifications within the scope and spirit of the present invention as defined by the appended claims.

What is claimed is:

1. A method of collecting a fluid sample using a sampling device having a tube which comprises a pliant material and having a sealed first end, a check valve connected at a second end of the tube, and a bouyancy-compensating ballast compartment, the tube defining an interior cavity, the method comprising:

lowering the sampling device into the fluid to be sampled while maintaining the check valve in the closed position;

moving the sampling device up and down to pump fluid into the tube, wherein the check valve is opened each time the sampling device is pulled upwards allowing fluid to enter the interior cavity;

filling up the interior cavity of the tube with fluid such that check valve closes and remains substantially closed against further movement when the cavity is substantially filled while submerged, thereby preventing additional fluid from entering the interior cavity; and pulling the sampling device out of the fluid.

2. The method of claim 1, wherein the check valve is biased into its closed position by means of a spring.

3. The method of claim 1, wherein the check valve closes each time the sampling device is moved down to thereby preclude fluid from entering the cavity while the sampling device is moved down.

4. The method of claim 3, wherein the check valve is closed by means of a spring.

5. The method of claim 1, wherein the buoyancy-compensating ballast compartment is filled with sand.

6. The method of claim 1, wherein the buoyancy-compensating ballast compartment is detachably secured to the first end of the tube.

7. The method of claim 1, wherein the check valve comprises a poppet valve.

8. The method of claim 1, wherein the check valve comprises a ball check valve.

9. The method of claim 1, wherein the check valve comprises a collapsing reed valve.

* * * * *